United States Patent [19]

van der Zel

[11] Patent Number: 5,453,290
[45] Date of Patent: Sep. 26, 1995

[54] DENTAL PROCELAIN, A METHOD OF PRODUCING A DENTAL RESTORATION, A DENTAL ALLOY

[75] Inventor: Joseph M. van der Zel, Zwaag, Netherlands

[73] Assignee: Elephant Edelmetaal B.V., Hoorn, Netherlands

[21] Appl. No.: 152,365

[22] Filed: Nov. 16, 1993

Related U.S. Application Data

[62] Division of Ser. No. 756,900, Sep. 9, 1991, abandoned.

[30] Foreign Application Priority Data

Sep. 10, 1990 [NL] Netherlands .................. 9001986

[51] Int. Cl.⁶ .................................................. A61C 13/083
[52] U.S. Cl. ................... 427/2.27; 427/2.26; 427/376.2; 427/377; 106/35; 433/207
[58] Field of Search .............. 427/2, 376.2, 376.3, 427/377, 2.26, 2.27; 501/5, 6, 16, 32; 106/35; 433/207

[56] References Cited

U.S. PATENT DOCUMENTS

| | | | |
|---|---|---|---|
| 1,283,264 | 10/1918 | Mowrey . | |
| 3,052,982 | 9/1962 | Weinstein | 433/213 |
| 3,585,064 | 6/1971 | Prosen | 427/380 |
| 3,666,540 | 5/1972 | Burnett . | |
| 4,008,080 | 2/1977 | Wagner | 75/134 N |
| 4,114,272 | 9/1978 | Saragossi | 427/2.27 |
| 4,125,442 | 11/1978 | Rogers | 427/376.4 |
| 4,132,830 | 1/1979 | Tsai | 427/2 |
| 4,455,383 | 6/1984 | Panzera | 501/6 |
| 4,522,783 | 6/1985 | Menicucci | 420/503 |
| 4,550,030 | 10/1985 | Ohi et al. | 427/2 |
| 4,604,366 | 8/1986 | Kacicz et al. | 501/6 |
| 4,661,071 | 4/1987 | Bell et al. | 427/2 |
| 4,689,197 | 8/1987 | Groll et al. | 427/2 |
| 4,798,536 | 1/1989 | Katz | 501/6 |
| 4,992,297 | 2/1991 | van der Zel | 427/2.27 |
| 5,221,207 | 6/1993 | Schoeck et al. | 433/207 |
| 5,240,172 | 8/1993 | Steinke et al. | 2.28/262.61 |
| 5,246,889 | 9/1993 | Kasuga et al. | 501/5 |

FOREIGN PATENT DOCUMENTS

| | | |
|---|---|---|
| 0155564 | 9/1985 | European Pat. Off. . |
| 0159205 | 10/1985 | European Pat. Off. . |
| 0225483 | 6/1987 | European Pat. Off. . |
| 2439012 | 5/1980 | France . |
| 1441346 | 12/1968 | Germany . |
| 1441336 | 4/1971 | Germany . |
| 2139331 | 2/1973 | Germany . |
| 2636039 | 2/1978 | Germany . |
| 2855739 | 6/1979 | Germany . |
| 2828304 | 9/1979 | Germany . |
| 2908203 | 9/1980 | Germany . |
| 3211703C2 | 12/1984 | Germany . |
| 249183 | 7/1994 | Germany . |
| 53-4720 | 1/1978 | Japan . |

OTHER PUBLICATIONS

Mackert, Jr., "Effects of Thermally Induced Changes . . . " from perspectives in Dental Ceramics, 1988, pp. 53–64 (no month available).

Mackert, Jr. et al, "The Effect of the Leucite Transformation on Dental Porcelain Expansion", 1986, pp. 32–36 (no month available).

*Primary Examiner*—Diana Dudash
*Attorney, Agent, or Firm*—Stevens, Davis, Miller & Mosher

[57] ABSTRACT

A system for dental restorations comprising dental alloys for the manufacture of a substructure of the restoration and dental porcelains for coating the substructure. The porcelains have a relatively high thermal expansion coefficient, above 14.5 μm/m.°C., and a relatively low firing temperature, below 950° C. The alloys have adapted properties, a thermal expansion coefficient above 14.5 μm/m.°C. and a solidus temperature of at least 1000° C.

17 Claims, No Drawings

DENTAL PROCELAIN, A METHOD OF PRODUCING A DENTAL RESTORATION, A DENTAL ALLOY

This is a division of application Ser. No. 07/756,900 filed Sep. 9, 1991, now abandoned.

This invention relates to a dental porcelain, to a method of producing a dental restoration such as a dental crown, inlay, bridge etc. comprising a substructure from a dental alloy which is at least partially coated with one or several layers of a fired-on dental porcelain, and to a dental alloy suitable for use therein.

This invention provides a metal-ceramic system in which a gold alloy having an aesthetic yellow colour is fired on with a dental porcelain tailored thereto. It is much appreciated in dentistry that a gold alloy on which porcelain may be fired too should have a yellow colour. This is connected with the wish not to fire porcelain about chewing surfaces in a metal ceramic restoration because of the high hardness of porcelain with respect to the natural teeth.

A distinction has hitherto always been made between the alloys derived from carat gold for casting all-metal restorations and alloys for the firing-on technique. Examples of conventional alloys for casting all-metal restorations are given in Table A below.

TABLE A

| Ex. No. | composition in wt. % | | | | | | | colour | solidus temp. °C. | expansion coeff. µm/m. °C. |
|---|---|---|---|---|---|---|---|---|---|---|
| | Au | Pt | Pd | Ag | Cu | Zn | In | | | |
| 1 | 70 | 5 | 2 | 13 | 9 | 1 | — | yellow | 900 | 16.4 |
| 2 | 67 | — | 4 | 15 | 13 | 1 | — | yellow | 895 | 16.5 |
| 3 | 58 | 1 | 4 | 24 | 12 | 1 | — | yellow | 920 | 17.3 |
| 4 | 52 | — | 10 | 32 | — | 2 | 4 | yellow | 950 | 16.8 |
| 5 | 42 | — | 10 | 26 | 21 | 1 | — | yellow | 860 | 17.2 |

Owing to the presence of copper and/or indium the above alloys have a thick dark oxide layer on which no porcelain can be fired because the bonding thereof to these alloys leaves something to be desired. Moreover, the above alloys have too low a solidus temperature (temperature at which the melting range begins) which endangers the stability of the metal structure during firing. It is well known that the firing temperature of the porcelain and the solidus temperature of the alloy for firing on must differ from each other by at least 50° C., preferably at least 100° C., in order to guarantee stability (avoidance of deformation of the metal structure). Because most of the porcelains applied have a firing temperature of about 950° C., none of these alloys satisfies this requirement.

For crowns, bridges, inlays, cone fittings, telescope restorations gold alloys have hitherto been used almost exclusively. Accordingly, as explained above, these alloys have too low a solidus temperature (of 850°–950° C.) to fire the conventional porcelain thereon.

In addition, the gold alloys applied in dentistry for all-metal restorations have a thermal expansion coefficient that is much too high to fire conventional porcelain thereon. It is well known that the thermal expansion coefficient of an alloy should not exceed that of the porcelain to be fired on by more than 1.5 µm/m.°C. (measured from 20° to 500° C.) in order to prevent fracture in the porcelain caused by too high stresses.

The thermal expansion coefficient of gold alloys for all-metal restorations is, measured from 20° to 500° C., in the range of from 16.4 to 18.0 µm/m.°C., while that of the conventional porcelains, measured from 20° to 500° C., is in the range of from 12.6 to 14.0 µm/m.°C.

In order yet to obtain gold alloys having a more or less yellow colour which are suitable for firing on the porcelains conventional at the present time, the copper and the silver are replaced in whole or in part by metals from the platinum group, particularly platinum and palladium, in order to increase the solidus temperature to a level which is higher than the firing temperature of the conventional porcelain by at least 50° C. and reduce the thermal expansion coefficient to from 13.8 to 14.7 µm/m.°C. (measured from 20° to 500° C.). The addition of palladium and platinum, however, has important consequences for the colour of the alloy. Palladium colours a gold alloy white at a content of 12%, while platinum gives gold an undesirable white colour at 18% addition to gold. In order yet to retain a yellow, albeit pale yellow, colour and satisfy the above requirements of thermal expansion, solidus temperature and physical properties (hardness, yielding point), the addition of platinum in these alloys is limited to 12% and that of palladium to 9%. When platinum and palladium are used in combination, the palladium+platinum content may not exceed 19%. These alloys, however, have a colour that cannot be compared with the deep yellow colour of the gold alloys applied for all-metal crowns. Some examples of well known gold alloys for firing on porcelain are shown in Table B below.

TABLE B

| Ex. No. | composition in wt. % | | | | | | colour | solidus temp. °C. | expansion coeff. µm/m. °C. |
|---|---|---|---|---|---|---|---|---|---|
| | Au | Pt | Pd | Ag | Sn | In | | | |
| 6 | 83 | 12 | 2 | 2 | — | 1 | pale yellow | 1100 | 14.5 |
| 7 | 84 | 8 | 5 | 1 | — | 2 | pale yellow | 1105 | 14.3 |
| 8 | 77 | 10 | 9 | 2 | 1 | 1 | pale yellow | 1145 | 13.9 |

Therefore, it has hitherto not been possible to fire porcelain about the gold alloys, highly appreciated because of their beautiful yellow colour, which are indeed largely used in the production of all-metal restorations. With the present invention, however, it has surprisingly been found possible to make a yellow gold alloy and a porcelain tailored thereto enabling porcelain to be fired on a hard yellow gold alloy.

The invention therefore provides in a first aspect a dental porcelain which is characterized by a thermal expansion coefficient, measured at a temperature of from 20° to 500° C., above 14.5 µm/m.°C. and a firing temperature below 950° C.

A preferred embodiment of this dental porcelain according to the invention is characterized by a thermal expansion coefficient, measured at a temperature of from 20° to 500° C., above 15.0 µm/m.°C. and a firing temperature below 900° C.

As will be further explained, the dental porcelain according to the invention is preferably prepared from at least three different glass compositions, including (a) one or more leucite-forming glass compositions having a thermal expansion coefficient, measured at a temperature of from 20° to 500° C., above 17.0 µm/m.°C., which consist essentially of 15–20 wt. % $Al_2O_3$, 13–19 wt. % $K_2O$, 0–5 wt. % $Na_2O$, balance $SiO_2$, additives and impurities, (b) one or more glass compositions having a thermal expansion coefficient, measured at a temperature of from 20° to 500° C., of 8.0–12.0 μm/m.°C., and a melting point of 750°–950° C., which consist essentially of 10–15 wt. % $Al_2O_3$, 4–7 wt. % $K_2O$, 6–15 wt. % $Na_2O$, 0–3 wt. % BaO, 0–3 wt. % $Li_2O$, balance $SiO_2$, additives and impurities, and (c) one or more low melting glass compositions having a melting point of 450°–700° C. which consist essentially of 0–5 wt. % $Al_2O_3$, 12–30 wt. % $Na_2O+K_2O$, 0–5 wt. % BaO, 0–5 wt. % $Li_2O$, balance $SiO_2$, additives and impurities. Preferably, such a dental porcelain is prepared from 50–80 wt. % of one or more glass compositions of type (a), 5–45 wt. % of one or more glass compositions of type (b), and 5–15 wt. % of a glass composition of type (c).

In another aspect the invention provides a method of producing a dental restoration such as a dental crown, inlay, bridge etc. comprising a substructure from a dental alloy which is at least partially coated with one or several layers of a fired-on dental porcelain, which process is characterized by applying a dental porcelain according to the invention as defined above.

Preferably, this method comprises the use of a dental alloy having a thermal expansion coefficient, measured at a temperature of from 20° to 500° C., which is higher than that of the dental porcelain by 0.5–1.5 μm/m.°C. and has a solidus temperature which is higher by at least 50° C., preferably at least 100° C., than the temperature at which the dental porcelain is fired on.

A preferred embodiment of such a process to be further explained is characterized in that dental porcelain is fired on while the dental restoration rests on a graphite plate and is shielded from the kiln atmosphere by means of a bell jar of quartz glass.

In a third aspect the invention provides a novel dental alloy which is characterized by a thermal expansion coefficient, measured at a temperature of from 20° to 500° C., above 14.5 μm/m.° C. and a solidus temperature of at least 1000° C.

Preferred is a dental alloy which is characterized by a thermal expansion coefficient, measured at a temperature of from 20° to 500° C., of 15–18 μm/m.°C. and a solidus temperature of 1000°–1200° C.

It is further preferred that the dental alloy is characterized by a composition consisting essentially of
40–80 wt. % Au;
15–50 wt. % Ag;
0–20 wt. % of Pd+Pt, with the understanding that when Pd and Pt are both present one of both is present at a content of not more than 4 wt. %;
0–5 wt. % in total of one or more elements from the group consisting of Zn, In, Sn, Ga, Ge, Al, Si and B;
0–5 wt. % in total of one or more elements from the group consisting of Ta, Ti and Re;
0–5 wt. % in total of one or more elements from the group consisting of Rh, Ir and Ru;
0–5 wt. % in total of one or more elements from the group consisting of Mo, Nb, W, Cr, Cu, Co, Ni and Fe;
0–3 wt. % in total of one or more elements from the group consisting of Sc, Y, La and the rare earths;
balance additives and impurities.

More in particular, a dental alloy is preferred according to the invention which is characterized by a composition consisting essentially of
45–75 wt. % Au;
20–40 wt. % Ag;
4–12 wt. % Pd and 0–2 wt. % Pt, or conversely, 4–12 wt. % Pt, and
0.2 wt. % Pd;
0.05–0.5 wt. % Ir;
0.5–2.0 wt. % Zn;
0–1.0 wt. % Sn;
0–0.5 wt. % Ta;
balance impurities.

Alloys according to the invention preferably contain from 40 to 80 wt. % gold, from 0 to 12 wt. % platinum and/or palladium, from 15 to 50 wt. % silver and a number of other elements influencing the desired properties of the alloy. The total amount of these other elements, however, is not more than 10 wt. %.

With this invention it is possible to fire porcelain about gold alloys which as to colour correspond to the conventional alloys for all-metal restorations. A dental technician can therefore use for all indications, both all-metal structures and metal-ceramic restorations, one alloy where he formerly needed at least two alloys. Moreover, for firing on he can now use an alloy showing a pleasant yellow colour on porcelain-free chewing surfaces.

Since gold is an expensive and scarce metal and the gold content in the alloys according to the invention can be reduced considerably as compared with the now existing yellow alloys for firing on, a considerable economic saving is obtained.

Since the alloys of the invention can be used for nearly all occurring dental restoration work, it is possible to carry out all restorations in a patient's mouth with one alloy. This prevents possible allergies and problems originating from galvanic tensions that may occur between alloys having a different composition in the mouth.

Because alloys according to the invention are yellow at a gold content of 50% while the conventional alloys with 50% gold (such a conventional alloy contains, e.g., 50% gold, 40% palladium, 8% indium, and 2% gallium) are white, the misunderstanding rather often arising between dentist and patient on the fact that a gold alloy should be yellow and not white will no longer occur because the gold alloy is now yellow indeed.

As a result of the relatively high silver content of the alloys according to the invention the colour of the oxidation layer is very light, in contrast to the hitherto conventional gold-platinum alloys for firing on. Thus the unaesthetic effect of a dark background showing through the porcelain is absent. Also the often occurring dark change, a dark oxidation edge between metal and ceramic is combined restorations, is absent with the alloys of the invention. Nevertheless, the alloys according to the invention show a surprisingly good bonding with porcelain.

A high silver content may ensure that in heat treatments required for the oxidation/degassing and firing-on cycles silver vapour is released in the partially evacuated (about 0.1 atm) kiln, which may cause damage to the heating elements of the kiln, resulting in their premature breakdown. However, it has now been found possible to remove these drawbacks by means of a special firing chamber. The firing chamber consists of a cylindrical quartz glass bell jar standing in a quartz glass tray with a raised edge. In the tray lies a thin round flat graphite plate on which the bottom edge of the cylindrical bell jar rests. The silver vapours are now absorbed by the graphite and can no longer reach the kiln space. Moreover, it has been found that the alloys according to the invention do not form an oxide layer when "oxidized" or degassed under the quartz glass bell jar.

Porcelain according to the invention at least consists of a frit having a high content of leucite crystals, a glass frit related to the matrix glassy phase of the leucite frit and an additional low melting glass frit which is not related to the residual melt of the high leucite frit but yet does not act aggressively on the leucite.

As compared with conventional porcelain the firing temperature is lower by at least 50° C. and the thermal expansion is sharply increased by the presence of a high leucite content. Moreover, the latter makes the porcelain stronger, until twice as strong as the conventional porcelains.

The combination of the alloy with the porcelain imposes special requirements on both materials:

a stable, very thin, optionally monomolecular oxidation layer which is very light in colour because of the absence of copper and tin. The oxidation layer has a good bonding with the underlying alloy;

a good metal-ceramic bond: the thin oxide layer which, moreover, properly adheres to the alloy gives an excellent porcelain-metal bond;

a good mutual adjustment of the thermal expansion coefficients of the metal and the ceramic: it is best if the alloy has a thermal expansion coefficient which is higher than that of the porcelain by 0.5 to 1.5 μm/m.°C. (measured from 20° to 500° C.) so that after cooling the porcelain is put under pressure which benefits the strength of the restoration.

The requirements which the above alloys according to the invention satisfy are as follows:

1. good flowability for completely filling the muffle chamber;
2. the melting interval is sufficiently above the firing temperature of the porcelain described here and yet low enough to be poured into existing casting equipment;
3. stable properly adhering oxide layer;
4. linear thermal expansion coefficient near that of the porcelain, preferably slightly above it;
5. adequate ceramic-metal bonding strength;
6. adequate strength at high temperature to resist the embedding mass during cooling;
7. adequate resistance to deformation at high temperature;
8. adequate mechanical and finishing properties;
9. free from oxide film;
10. low content of volatile elements;
11. controlled isotropic solidification shrinkage;
12. gas-free casting showing no porosity;
13. minimum segregation during crystallization;
14. a composition that can be easily soldered.

The two most important requirements for a reliable metal-ceramic combination are as follows:

1. Thermal compatibility of ceramic and metal over the range from the glass transformation temperature of the ceramic (about 500° C.) to room temperature because of adapted expansion coefficients of metal and ceramic;
2. Achievement of a good metal-ceramic bond.

Thermal compatibility

A difference in thermal expansion coefficients is an important parameter in predicting metal-ceramic compatibility. In general, it applies that the alloy must have a higher thermal expansion coefficient than the ceramic so as to create compressive stress in the ceramic during cooling.

The adaptation of the thermal expansion coefficient of metal-ceramic to the desired level, which is close to but slightly lower than the metal-ceramic alloys, is determined by the crystallization process of leucite in the ceramic. The separation of leucite causes an increase in the thermal expansion of the ceramic which in the first instance consists substantially of a glassy phase. Depending on the viscosity of the glassy phase which, in turn, depends on the firing temperature, the thermal expansion will remain constant during repeated firing with a proper equilibrium of the composing frits.

It has now been found that this can be achieved by combining three different types of frits. For that matter, it is already proposed in U.S. Pat. No. 3,052,982 of Weinstein to compose a porcelain from different frits. This patent describes a technique for preparing a porcelain to be fired on alloys, the expansion of the porcelain, by means of a combination of two different frits, being adjusted such that the porcelain is compatible with the alloy used for firing on the porcelain. The porcelain is produced from specific amounts of feldspars and glass which determine the physical properties of the porcelain.

Although the above technique has been used with some success, it often results in porcelain varying as regards properties according as there is fired several times. The present invention, however, provides a porcelain which shows a high stability in expansion.

In order to meet all requirements of thermal expansion, low firing temperature and thermal expansion stability, at least three different frits are applied according to the invention. At least one of these frits is a so-called high leucite frit in which, by means of a heat treatment, leucite crystallizes out of a glass, leaving a matrix which is relatively deficient in aluminium oxide and potassium oxide. When adding to this frit a second frit which as regards composition is closely related to the matrix of the high leucite frit, no interaction takes place between the two frits and the thermal expansion does not change. Because of the relatively high melting point of the high leucite frit it is not possible to lower the firing temperature of the final porcelain by adding the glass frit without also reducing the thermal expansion coefficient to too low a value. Also when adding an excess of glass frit with respect to the high leucite frit, there cannot be attained a firing temperature substantially lower than 950° C. Also when the glass frit is allowed to slightly deviate from the matrix of the high leucite frit by adding oxides which further lower the melting point of the glass frit, no acceptable product is obtained because the low melting glass frit acts very aggressively on the high leucite frit, the result being an unstable product.

The porcelain described in the present application therefore contains at least three different types of frits, namely in addition to at least a high leucite frit and at least a glass frit complementary to the leucite frit also a low melting frit having such a composition that it does not affect the stability of the thermal expansion of the porcelain, considerably decreases the melting point and yet does not reduce the thermal expansion too much. A composition satisfying these conditions is found in a frit having a relatively high sodium oxide+potassium oxide content, a relatively low aluminium oxide content and a relatively high barium oxide content as compared with the conventional complementary glass frits, in such a ratio that the melting point of the frit is lower than about 700° C. and the thermal expansion coefficient is about 13 μm/m.°C. Surprisingly, it has been found that such a frit shows no aggressiveness with respect to the high leucite frit(s) and actually causes a desired decrease of the firing temperature and a high thermal expansion coefficient.

In order to meet all requirements of thermal expansion, low firing temperature and stability of thermal expansion, a high leucite frit substantially having a composition of 58–67 wt. % $SiO_2$, 15–20 wt. % $Al_2O_3$, 13–19 wt. % $K_2O$, 0–5 wt. % $Na_2O$, a frit more or less complementary to the matrix thereof and a low melting frit are mixed with each other in a ratio of, e.g., 80:10:10 or of 55:35:10. An example of a suitable combination of frits is shown in Table C below.

TABLE C

| Frit component | high leucite | glass frit | lowmelting |
| --- | --- | --- | --- |
| $SiO_2$ | 63 | 69 | 70 |
| $Al_2O_3$ | 18 | 12 | 3 |
| $K_2O$ | 16 | 6 | 10 |
| $Na_2O$ | 3 | 8 | 10 |
| BaO | — | 3 | 4 |
| $Li_2O$ | — | 2 | 3 |
| Therm. exp. (in μm/m. °C., measured from 20–500° C.) | 18.5*) | 9.8 | 13.0 |
| Proportion (wt. %) | 70 | 20 | 10 |

*)After a heat treatment of 1 hour at 900° C.

The ceramic composed according to the invention, such as the ceramic shown in Tables C and G, exhibits some increase in leucite content if the ceramic is kept at a temperature of 800° C. (annealing) or if it is cooled slowly after firing. Because of this effect the expansion of the ceramic can be adapted as much as possible to that of the alloy (Table D).

TABLE D

Thermal expansion coefficient (μm/m. °C.) of porcelain according to the invention.

| Pretreatment | After 1 firing | After 5 firings | After heat treatment 10 min. 800° C. |
| --- | --- | --- | --- |
| Opaque | 15.8 | 15.7 | 16.2 |
| Dentin | 15.3 | 15.3 | 15.9 |

The increase in thermal expansion of the porcelain given by way of example can be reversed by one more firing and normally cooling.

Foreign particles such as opacifiers, e.g., $SnO_2$ and $TiO_2$, and the crystalline leucite may inhibit any further cracking to some extent, thus increasing the strength of the ceramic. Increasing the leucite content enables a significant increase in bending strength, e.g. from 60 $N/mm^2$ to 90 $N/mm^2$.

Metal-ceramic bond

Despite the large amount of scientific articles of the past twenty years concerning metal-ceramic bond the dental profession has not yet been able to lay down a universally accepted bonding test. The main objections are the lack of correlation with clinical experiences and the possibility that often the strength of the ceramic itself is measured rather than the bonding strength at the metal-ceramic interface. Furthermore, residual stresses occurring in the ceramic during cooling after firing on play an important role. Therefore, it seems better to use a typification of the fracture, instead of the numerical values of a test.

The chemical composition (wt. %) of some examples of alloys according to the invention are given in Table F.

A round disk of the alloys was cast with a diameter of 25 mm and a thickness of 1.0 mm. After casting the castings were ground with coarse and fine aluminium oxide stones. Then they were blasted with non-recyclable 50 μm $Al_2O_3$ and cleaned in distilled water in an ultrasonic bath for 10 min. The oxidation treatment was carried out in a standard porcelain kiln.

After oxidation with the aid of a plastic mould first 0.2 mm opaque porcelain and then 0.8 mm translucent porcelain were applied and fired at 880° C. under vacuum. The firing scheme is given in Table E.

TABLE E

The firing scheme used in the bonding tests.

| Porcelain layer | Starting temp. °C. | Final temp. °C. | Rate of increase °C./min | Time at final temp. min |
| --- | --- | --- | --- | --- |
| Opaque porcelain | 500 | 890 | 50 | 1 |
| Transl. porcelain | 500 | 880 | 50 | 1 |

The metal-ceramic disk, with the porcelain directed downwards, was deformed from the top by a die having a spherical end. The disk was bent 0.4 mm in the centre to obtain a consistent deformation of the disk and removal of the ceramic with a minimum of cracks in the metal. After breaking off the porcelain, loose particles of porcelain were removed from the fracture surface with a nylon brush and the porcelain was placed in an ultrasonic bath for 10 minutes.

After breaking the samples were examined with a scanning electron microscope for the amount of remaining porcelain surface. The percentage of oxidized metal surface still coated with ceramic was measured by measuring the amount of silicon on the fracture surface by means of E.D.A.X. and comparing it with the uncovered portion of metal surface and a 100% covering porcelain surface.

The average surface fraction of remaining ceramic is given in Table F. The values for remaining surface still covered with porcelain show that most of it still adheres to the alloy after breaking the mass off the porcelain. Tests on other alloy systems have shown that a percentage above 50% does not lead to practical problems.

Before a chemical bond is possible the ceramic must moisten the metal surface. Moistening of a metal by a molten glass depends on the reduction of the surface energy of the metal surface by the liquid glass and is considered good if the angle of contact is about 90°. A smaller angle is a condition for obtaining a proper bond. In general, the presence of an oxide layer has a favourable effect. In order to promote the moistening necessary for bonding the presence of a low melting phase in the porcelain is important. The glass in the covering porcelain is capable of dissolving most of the oxide until only a layer of a few molecules is left between ceramic and metal. In general, the glass is not capable of dissolving all the oxide of the metal surface so that a clear oxide layer remains present between ceramic and metal. When during repeated heating the oxide layer increases progressively, the bond between the oxide layer and the metall may be lost. Because the alloys of the invention contain no elements giving a thick oxide layer and because the alloys have a high silver content, no thick oxide layer is formed at the outside of the alloy. Silver gives rise to internal oxidation rather than to external oxidation. Thus there will remain an oxide anchored by internal oxidation, which oxide provides a proper bond.

The addition of not more than 5 wt. % rhodium, ruthenium and/or iridium (preferably not more than 2 wt. %) gives the alloy a fine-grained structure. Chromium, copper, cobalt, nickel and/or iron when added in an amount up to 5 wt. % may give an increase in strength. Tantalum, titanium and rhenium when added in an amount up to 5 wt. %

(preferably not more 2 wt. %) likewise increase the strength of the alloy and additionally have a grain refining effect. In view of protecting the alloys against oxidation during the melting process, it has been found that addition up to 5 wt. % zinc, indium, tin, gallium, germanium, aluminium, silicon and/or barium may be advantageous. Zinc is preferred here because this element rather rapidly leads to a proper hardening. In order not to allow the melting point to fall too much, the addition thereof is preferably limited to not more than 2 wt. %. For the same reason addition of not more than 3 wt. % scandium, yttrium, lanthanum and other rare earths reduce the oxidation of the alloys.

EXAMPLE 1

In a crucible of pure alumina in a vacuum induction furnace the following metals were weighed in and molten under a partial pressure of 400 torr of argon gas and then cast into a bar in a shape which was already present in the vacuum chamber: 70 wt. % gold, 6 wt. % palladium, 1 wt. % platinum, 0.1 wt. % iridium, 1.2 wt. % zinc, 0.5 wt. % tin, and 21.2 wt. % silver (see Table F). After casting the mould was removed from the vacuum induction furnace and the mould was opened.

The bar was rolled out into a sheet, optionally with intermediate annealing to return the sheet to a rollable state. Then the sheet was cut to pieces and the alloy was cut to cubes.

Subsequently, the alloys were poured into an electric casting apparatus at 1280° C. in a graphite-containing phosphate-bound embedding mass mould which was preheated to 750° C.

The porcelain was made in the conventional manner but consisted of 2 high leucite frits (together 70 wt. %), 2 glass frits (together 20 wt. %) and 10 wt. % of a special low melting glass frit (see Table G).

The bonding with porcelain is shown in Table F.

EXAMPLES 2–4

In the same manner as in Example 1 the other alloys shown in Table F were produced. Example 4 is included herein to show that the simultaneous addition of platinum and palladium results in a decrease of strength. This is caused by segregation of the platinum metals, resulting in that they can no longer contribute to the strength.

The chemical composition (in wt. %) of the alloys according to the invention prepared in these examples is given in Table F.

TABLE F

| Alloys according to the invention | | | | |
|---|---|---|---|---|
| Metal component | 1 | 2 | 3 | 4 |
| Gold | 70 | 50 | 50 | 50 |
| Palladium | 6 | 10 | 1 | 8 |
| Platinum | 1 | 1 | 10 | 5 |
| Iridium | 0.1 | 0.1 | 0.1 | 0.1 |
| Zinc | 1.3 | 1.4 | 1.1 | 2 |
| Tin | 0.5 | 0.5 | 0.5 | 0.5 |
| Silver | 21.1 | 36.8 | 37.1 | 34.3 |
| Tantalum | — | 0.2 | 0.2 | — |
| Ruthenium | — | — | — | 0.1 |
| Vickers hardness, HV | 230 | 230 | 180 | 90 |
| Tensile strength, MPa | 546 | 662 | 444 | 310 |
| Yielding point, MPa | 497 | 513 | 331 | 190 |
| Elongation at break, % | 5.2 | 7.8 | 11.8 | 22 |
| Melting interval, °C. | 1040– | 1050– | 1030– | 1020 |

TABLE F-continued

| Alloys according to the invention | | | | |
|---|---|---|---|---|
| Metal component | 1 | 2 | 3 | 4 |
| Thermal expansion coefficient (20–500° C.) μm/m. °C. | 1100 16.4 16.2 | 1110 16.8 | 1100 17.0 | 1090 |
| Oxidation colour Colour | pale gray yellow | yellow pale yellow | yellow yelloy | yellow yellow |
| Porcelain bonding, % | 65 | 69 | 71 | 61 |

According to a preferred embodiment a porcelain suitable for these alloys consists of five frits. After melting at 1500° C., quenching in water and grinding to finer than 75 μm, frits 1 and 2 were treated at a temperature of 900° C. for 1 hour to crystallize out leucite ($K_2O.Al_2O_3.3SiO_2$). The expansion thus increased from about 9 to about 17 for frit 1 and about 19 for frit 2. Frits 3, 4 and 5 were molten at 1300° C., quenched in water and ground until everything was finer than 75 μm.

TABLE G

| Porcelain according to the invention | | | | | |
|---|---|---|---|---|---|
| Frit component | high leucite | | glass frit | | low melting |
| Frit No. | 1 | 2 | 3 | 4 | 5 |
| $SiO_2$ | 65 | 61 | 71 | 67 | 65 |
| $Al_2O_3$ | 17 | 19 | 11 | 13 | 6 |
| $K_2O$ | 15 | 17 | 5 | 6 | 11 |
| $Na_2O$ | 3 | 3 | 8 | 9 | 11 |
| BaO | — | — | 3 | 3 | 4 |
| $Li_2O$ | — | — | 2 | 2 | 3 |
| Melting point, °C. | 1050 | 1100 | 880 | 850 | 650 |
| Therm. exp. μm/m. °C. (from 20–500° C.) | 17*) | 19*) | 8.9 | 9.8 | 13 |
| Proportion, wt. % | 35 | 35 | 10 | 10 | 10 |

*)After a heat treatment of 1 hour at 900° C.

What I claim is:

1. A method of producing a dental restoration comprising a substructure of a dental alloy which is at least partially coated with one or several layers of a fired-on dental porcelain, which process comprises firing a dental porcelain having a thermal expansion coefficient, measured at a temperature of about 20° to 500° C., above 14.5 μm/m/°C. and a firing temperature below 950° C., onto the substructure of dental alloy, said dental alloy having a thermal expansion coefficient, measured at a temperature of from 20° to 500° C., which is higher than that of the dental porcelain by 0.5–1.5 μm/m/°C., and having a solidus temperature which is higher by at least 50° C. than the temperature at which the dental porcelain is fired on.

2. The method as claimed in claim 1, wherein said dental porcelain has a thermal expansion coefficient, measured at a temperature of from 20° to 500° C., above 15.0 μm/m/°C. and a firing temperature of below 900° C.

3. The method as claimed in claim 1, wherein said solidus temperature of said dental alloy is at least 100° C. above the firing temperature.

4. The method as claimed in claim 1, wherein said dental alloy consists essentially of (a) 40–80 wt % Au;

(b) 15–50 wt % Ag;

(c) 0–20 wt % of Pd+Pt, with the understanding that when Pd and Pt are both present one of both is present at a content of not more than 4 wt %;

(d) 0–5 wt % in total of one or more elements selected from the group consisting of Zn, In, Sn, Ga, Ge, Al, Si and B;

(e) 0–5 wt % in total of one or more elements selected from the group consisting of Ta, Ti and Re;

(f) 0–5 wt % in total of one or more elements selected from the group consisting of Rh, Ir and Ru;

(g) 0–5 wt % in total of one or more elements selected from the group consisting of Mo, Nb, W, Cr, Cu, Co, Ni and Fe; and (h) 0–3 wt % in total of one or more elements selected from the group consisting of Sc, Y, La and the rare earths; wherein the weight percentages mentioned in (a)–(h) total 100%.

5. The method as claimed in claim 1, wherein said dental alloy consists essentially of (a) 45–75 wt % Au;

(b) 20–40 wt % Ag;

(c) Pd and Pt, wherein one of Pd and Pt is present in an amount of 4–12 wt % and the other is present in an amount of 0–2 wt %;

(d) 0.05–0.5 wt % Ir;

(e) 0.5–2.0 wt % Zn;

(f) 0–1.0 wt % Sn; and (g) 0–0.5 wt % Ta;

wherein the weight percentages mentioned for (a)–(g) total 100%.

6. The method according to claim 1, wherein the firing is conducted in a kiln having an atmosphere and, during said firing, the dental restoration rests on a graphite plate and is shielded from the kiln atmosphere by means of a bell jar of quartz glass.

7. The method according to claim 1 wherein the dental restoration produced is selected from the group consisting of a dental crown, inlay and bridge.

8. A method of producing a dental restoration comprising a substructure of a dental alloy which is at least partially coated with one or several layers of a fired-on dental porcelain, which process comprises firing a dental porcelain having a thermal expansion coefficient, measured at a temperature of about 20° to 500° C., above 14.5 μm/m/°C. and a firing temperature below 950° C., onto the substructure of dental alloy, said dental alloy having a thermal expansion coefficient, measured at a temperature of from 20° to 500° C., which is higher than that of the dental porcelain by 0.5–1.5 μm/m/°C., and having a solidus temperature which is higher by at least 50° C. than the temperature at which the dental porcelain is fired on; said dental porcelain being prepared from at least three different glass compositions, including (a) one or more leucite-forming glass compositions having a thermal expansion coefficient, measured at a temperature of from 20° to 500° C., above 17.0 μm/m/°C.;

(b) one or more glass compositions having a thermal expansion coefficient, measured at a temperature of from 20° to 500° C. of 8.0–12.0 μm/m/°C. and a melting point of 750°–950° C; and (c) one or more low melting glass compositions having a melting point of 450°–700° C.

9. The method as claimed in claim 8, wherein the leucite-forming glass compositions (a) consist essentially of 15–20 wt. % $Al_2O_3$, 13–19 wt. % $K_2O$, 0–5 wt. % $Na_2O$, balance $SiO_2$; the glass compositions (b) consist essentially of 10–15 wt. % $Al_2O_3$, 4–7 wt. % $K_2O$, 6–15 wt. % $Na_2O$, 0–3 wt. % BaO, 0–3 wt. % $Li_2O$, balance $SiO_2$ ; and the low melting glass compositions (c) consist essentially of 0–5 wt. % $Al_2O_3$, 12–30 wt. % $Na_2O+K_2O$, 0–5 wt. % BaO, 0–5 wt. % $Li_2O$, balance $SiO_2$.

10. The method as claimed in claim 8, wherein said dental porcelain is prepared from 50–80 wt. % of glass composition (a), 5–45 wt. % of glass composition (b), and 5–15 wt. % of low melting glass composition (c).

11. The method as claimed in claim 8, wherein said dental alloy consists essentially of (a) 45–75 wt % Au;

(b) 20–40 wt % Ag;

(c) Pd and Pt, wherein one of Pd and Pt is present in an amount of 4–12 wt % and the other is present in an amount of 0–2 wt %;

(d) 0.05–0.5 wt % Ir;

(e) 0.5–2.0 wt % Zn;

(f) 0–1.0 wt % Sn; and (g) 0–0.5 wt % Ta;

wherein the weight percentages mentioned for (a)–(g) total 100%.

12. The method according to claim 8, wherein the firing is conducted in a kiln having an atmosphere and, during said firing, the dental restoration rests on a graphite plate and is shielded from the kiln atmosphere by means of a bell jar of quartz glass.

13. The method according to claim 8, wherein the dental restoration produced is selected from the group consisting of a dental crown, inlay and bridge.

14. The method as claimed in claim 8, wherein said dental porcelain has a thermal expansion coefficient, measured at a temperature of from 20° to 500° C., above 15.0 μm/m/° C. and a firing temperature of below 900° C.

15. The method as claimed in claim 8, wherein said solidus temperature of said dental alloy is at least 100° C. above the firing temperature.

16. The method as claimed in claim 8, wherein said dental alloy consists essentially of (a) 40–80 wt % Au;

(b) 15–50 wt % Ag;

(c) 0–20 wt % of Pd+Pt, with the understanding that when Pd and Pt are both present one of both is present at a content of not more than 4 wt %;

(d) 0–5 wt % in total of one or more elements selected from the group consisting of Zn, In, Sn, Ga, Ge, Al, Si and B;

(e) 0–5 wt % in total of one or more elements selected from the group consisting of Ta, Ti and Re;

(f) 0–5 wt % in total of one or more elements selected from the group consisting of Rh, Ir and Ru;

(g) 0–5 wt % in total of one or more elements selected from the group consisting of Mo, Nb, W, Cr, Cu, Co, Ni and Fe; and (h) 0–3 wt % in total of one or more elements selected from the group consisting of Sc, Y, La and the rare earths;

wherein the weight percentages mentioned in (a)–(h) total 100%.

17. A method of producing a dental restoration comprising a substructure of a dental alloy which is at least partially coated with one or several layers of a fired-on dental porcelain, which process comprises firing a dental porcelain having a thermal expansion coefficient, measured at a temperature of about 20° to 500° C., above 14.5 μm/m/°C. and a firing temperature below 950° C., onto the substructure of dental alloy, said dental alloy having a thermal expansion coefficient, measured at a temperature of from 20° to 500° C., which is higher than that of the dental porcelain by 0.5–1.5 μm/m/°C., and having a solidus temperature which is higher by at least 50° C. than the temperature at which the dental porcelain is fired on; said dental alloy having a thermal expansion coefficient, measured at a temperature of from 20° to 500° C., of 15–18 μm/m/°C. and a solidus temperature of 1000°–1200° C.

* * * * *